United States Patent
Ibert et al.

(10) Patent No.: US 9,598,325 B2
(45) Date of Patent: Mar. 21, 2017

(54) METHOD FOR STABILIZING A COMPOSITION CONTAINING AT LEAST ONE PRODUCT OF INTERNAL DEHYDRATION OF A HYDROGENATED SUGAR, RESULTING COMPOSITION AND USES THEREOF

(71) Applicant: ROQUETTE FRERES, Lestrem (FR)

(72) Inventors: Mathias Ibert, La Chapelle D'armentieres (FR); Herve Wyart, Cuinchy (FR); Patrick Fuertes, Lomme (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/787,899

(22) PCT Filed: Apr. 30, 2014

(86) PCT No.: PCT/FR2014/051043
§ 371 (c)(1),
(2) Date: Oct. 29, 2015

(87) PCT Pub. No.: WO2014/177815
PCT Pub. Date: Nov. 6, 2014

(65) Prior Publication Data
US 2016/0083310 A1    Mar. 24, 2016

(30) Foreign Application Priority Data
May 2, 2013  (FR) ..................... 13 54034

(51) Int. Cl.
| | |
|---|---|
| *C04B 14/00* | (2006.01) |
| *C04B 24/00* | (2006.01) |
| *C07B 63/04* | (2006.01) |
| *C07D 493/04* | (2006.01) |
| *A61K 31/70* | (2006.01) |

(52) U.S. Cl.
CPC ............ *C07B 63/04* (2013.01); *C07D 493/04* (2013.01); *A61K 31/70* (2013.01)

(58) Field of Classification Search
None
See application file for complete search history.

(56) References Cited

U.S. PATENT DOCUMENTS

| | | | |
|---|---|---|---|
| 4,564,692 A | 1/1986 | Feldmann et al. | |
| 4,861,513 A | 8/1989 | Lueders et al. | |
| 6,811,604 B2 * | 11/2004 | Mentink ................ | C04B 24/02 106/729 |
| 2003/0032832 A1 | 2/2003 | Shahid | |
| 2003/0097028 A1 | 5/2003 | Fuertes | |
| 2004/0110969 A1 | 6/2004 | Fleche et al. | |
| 2014/0031514 A1 | 1/2014 | Namiki et al. | |

FOREIGN PATENT DOCUMENTS

| | | |
|---|---|---|
| CA | 1 178 288 A | 11/1984 |
| EP | 0 323 994 B1 | 3/1993 |
| EP | 1 446 373 B1 | 8/2010 |
| GB | 613 444 A | 11/1948 |
| WO | 01/94352 A1 | 12/2001 |
| WO | 03/043959 A1 | 5/2003 |
| WO | 2012/133850 A1 | 10/2012 |

OTHER PUBLICATIONS

International Search Report, dated Jul. 7, 2014, from corresponding PCT application.

* cited by examiner

*Primary Examiner* — Patrick Lewis
(74) *Attorney, Agent, or Firm* — Young & Thompson

(57) ABSTRACT

A method for improving the stability of compositions of a product for internal dehydration of a hydrogenated sugar, in particular an isosorbide composition, the method involving the use of monoethanolamine, diethanolamine, triethanolamine and the mixtures thereof as a stabilization agent. The resulting compositions and their various uses thereof are also described.

11 Claims, No Drawings

METHOD FOR STABILIZING A COMPOSITION CONTAINING AT LEAST ONE PRODUCT OF INTERNAL DEHYDRATION OF A HYDROGENATED SUGAR, RESULTING COMPOSITION AND USES THEREOF

The present invention relates to a method which makes it possible to improve the storage-stability of compositions of an internal dehydration product of a hydrogenated sugar, in particular an isosorbide composition, said method being based on the use of monoethanolamine, diethanolamine, triethanolamine and mixtures thereof as a stabilizing agent. It also relates to the resulting compositions and to the various uses thereof.

Exploiting our renewable biological resources has become a major ecological and economic imperative in the face of the exhaustion and the increase in prices of fossil materials such as oil. The development of 1,4:3,6-dianhydrohexitols falls within this context.

These products, also called isohexides, are obtained by internal dehydration of $C_6$ hydrogenated sugars (hexitols) such as sorbitol, mannitol and iditol. In the present application, the term "dianhydrohexitols" encompasses isosorbide (1,4-3,6-dianhydrosorbitol), isomannide (1,4-3,6-dianhydromannitol) and isoidide (1,4-3,6-dianhydroiditol) having the following formulae, and also mixtures of these products:

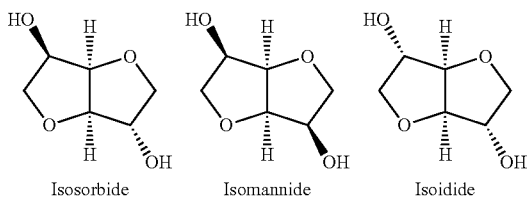

Isosorbide          Isomannide          Isoidide

A strong industrial development potential exists currently for isohexides, and in particular for isosorbide, the use of which is envisioned for the preparation:
- of isosorbide 2-nitrate, 5-nitrate or 2,5-dinitrate, of use in the therapeutic treatment of diseases, in particular cardiac and/or vascular diseases;
- of alkylated, in particular dimethylated, derivatives of isosorbide, of use in particular as solvents in the context of the preparation of pharmaceutical or cosmetological compositions;
- of isosorbide derivatives intended for detergent compositions for fuels,
- of alkylated or alkenylated derivatives that can be used as plasticizers for polymers, for adhesives or for inks;
- of particular biphosphites that can be used as stabilizing agents for polymers or lubricants;
- of articles based on polyvinyl alcohol, on polyurethanes, or on polymers and copolymers such as polyesters and polycarbonates;
- of biodegradable polycondensates;
- of aqueous lacquers or of compositions with a surface-covering and/or -coloring action.

For the majority of the abovementioned applications of isosorbide and other internal dehydration products of hydrogenated sugars, in particular of the other isohexides, it is generally required to apply a purification treatment to the compositions resulting directly from the actual dehydration step. This is because, in particular, any hydrogenated sugar subjected to such a step (for example sorbitol) is capable, during said step, of being converted, as well as into the desired dehydration product (for example isosorbide), into various co-products such as:
- isomers of said desired product, for example isomers of isosorbide such as isomannide and isoidide,
- products that are less dehydrated than the desired product or than its isomers, for example sorbitan, mannitan or iditan,
- derivatives resulting from the oxidation or more generally from the degradation of the abovementioned products, it being possible for these derivatives to include, for example when the desired product is isosorbide, co-products of deoxy monoanhydrohexitol, monoanhydropentitol, monoanhydrotetritol, anhydrohexose, hydroxymethylfurfural or glycerol type,
- derivatives resulting from the polymerization of the abovementioned products, and/or strongly colored species, of poorly defined nature.

It should be recalled that, generally, all or some of these various categories of co-products or impurities are generated to a greater or lesser degree during the actual step of dehydration of the hydrogenated sugar, this being independently of the conditions and precautions implemented in practice during said step, and for example independently: of the nature and presentation form of the acidic dehydration catalyst used (inorganic acid, organic acid, cationic resin, etc.), or of the amount of water or of organic solvent(s) in the initial reaction medium, or of the purity of the hydrogenated sugar, for example sorbitol, composition used as raw material.

Thus, there is an entire section of the literature dedicated to technologies aimed at obtaining compositions resulting from said dehydration step, which are improved in terms of purity, this being by adjusting the reaction conditions during said step, or by applying one or more purification treatment(s) after said step, or else by combining these various means.

In the first category, mention may be made of patent CA 1 178 288 which recommends (page 14, lines 3-8) carrying out the dehydration reaction under an inert gas atmosphere in order to prevent oxidation reactions, in particular when relatively high reaction temperatures and relatively long reaction times are envisioned. Patent U.S. Pat. No. 4,861,513 is also along these lines, describing a sorbitol dehydration reaction carried out in the simultaneous presence of inert gas (nitrogen) and of a reducing agent (sodium hypophosphite) for the purpose of preparing mixtures of particular polyols, which have a low dianhydrosorbitol content (10% to 26% by dry weight).

In the second category, reference may be made to patent U.S. Pat. No. 4,564,692 which mentions, without in any way providing details thereof, the prepurification, on ionic exchangers and/or active carbon, of isosorbide or isomannide compositions and then, after concentration by evaporation and inoculation of crystals of the desired isohexide, the crystallization thereof from water. Patent WO 01/94352, which teaches a purification by treatment with an ionic exchange means, and then a decolorizing means, may also be indicated.

Finally, in the third category, mention may be made of patent GB 613 444 which describes the obtaining, by dehydration in a water/xylene medium, of an isosorbide composition subsequently subjected to a treatment of distillation and then recrystallization from an alcohol/ether mixture. With regard to patent EP 0 323 994, it envisages the use of particular dehydration catalysts (respectively a gaseous hydrogen halide and liquid hydrogen fluoride) advantageously combined with carboxylic acids as co-catalysts, then distillation of the resulting crude isosorbide or isomannide compositions.

Contrary to this prior art, the applicant had then made the double observation that the level of stability of an isohexide composition did not correlate with its level of purity, but that the use of an agent such as nitrogen gas or sodium borohydride as described in the prior art (at the latest at the time of the distillation step) did not make it possible to significantly improve this stability.

It is while further continuing its studies that the applicant company had then found, surprisingly and unexpectedly, that only a) particular stabilizing agents, in the case in point in non-gaseous form b) used at a particular time in the preparation process, in the case in point after the actual distillation step, made it possible to prepare isohexide compositions of which the behavior with respect to storage, at the very least at ambient or moderate temperature, was improved.

This invention was the subject of patent EP 1 446 373, protecting a method for preparing a composition of internal dehydration product of a hydrogenated sugar, characterized in that it comprises:
a) a step of distilling a medium containing said internal dehydration product in order to obtain a distillate enriched in this product,
b) optionally, at least one subsequent step of purifying the distillate thus obtained,
c) a subsequent step of bringing the distillate obtained during step a), and then optionally subjected to step b), into contact with an agent capable of improving the stability of the internal dehydration product predominantly contained in the distillate, said agent not being in gaseous form,
d) optionally, a subsequent step of shaping the resulting composition of internal dehydration product of a hydrogenated sugar.

Said document relates to a certain number of possibilities for the improving agent used during step c), and which can be chosen from:
reducing agents, and in particular compounds based on boron or on aluminum, such as sodium borohydride ($NaBH_4$) or lithium aluminum hydride ($LiAlH_4$);
compounds based on phosphorus, such as a phosphine or a phosphite;
antioxidants, and in particular compounds based on nitrogen, in particular aromatic or non-aromatic amines, optionally containing, moreover, at least one alcohol function, such as hydroxylamine, morpholine, and derivatives thereof;
nitrogenous or non-nitrogenous aromatic compounds, optionally containing at least one alcohol function, for instance hydroquinone, phenol, tocopherols and respective derivatives thereof;
antioxidant compounds based on phosphorus or on sulfur, such as phosphites, phosphonites, sulfites, the salts of esters of thiodipropionic acid and mixtures thereof;
anti-acid agents;
metal-deactivating agents, such as metal-complexing or -chelating agents of natural origin;
products authorized as food additives, in particular those termed antioxidants, acidity regulators or sequestrants within the meaning of the European regulations, such as ascorbic acid (vitamin C), erythorbic acid, lactic acid, citric acid, gallic acid, tocopherols, derivatives (in particular salts) of all these products, BHT, butylated hydroxyanisole (BHA) and any mixtures of these products.

The applicant company then demonstrated that, through the implementation of such a method, particularly stable compositions were obtained. The term "stable composition" within the meaning of document EP 1 446 373 is intended to mean a composition which, when stored in a non-inert atmosphere for a period of at least one month and at a temperature of 40° C., has both a formic acid content of less than 0.0005% and an overall monoanhydrohexose content of less than 0.005%, these percentages being expressed by dry weight relative to the dry weight of said composition.

This stability is, for the compositions obtained by virtue of the abovementioned method, greater than 1 month and can reach at least 2 months, preferably at least 6 months and even more preferentially at least one year. As improving agent used during step c), patent EP 1 446 373 exemplifies sodium borohydride, morpholine, BHT, vitamin C, sodium borate, sodium hydroxide and disodium phosphate, the best results (stability of 6 months) being obtained for sodium borohydride and morpholine.

As it happens, working to improve the method that it had developed, in particular in terms of increasing the duration of stability of a composition of internal dehydration product with a hydrogenated sugar, the applicant has at the current time, after numerous research studies, achieved such a result. The latter is, inter alia, based on the identification of a parameter which has an essential role on the abovementioned stability, but also on the adjustment of this parameter.

In the case in point, the present application illustrates the influence of the nature of the improving agent introduced in step c) of the method according to document EP 1 446 373, and that the particular choice of monoethanolamine, diethanolamine, triethanolamine or mixtures thereof produced particularly advantageous results in terms of extension of the duration of stability of the compositions envisioned. These results are supported by monitoring the pH of such compositions over time, said parameter being known to be directly linked to the stability of said compositions, as indicated in the abovementioned patent. In this respect, a notable shift or change in the pH signifies a loss of the degree of stability of such compositions.

Thus, a practical and reliable means for evaluating the stability of such compositions is to monitor the change in their pH, after having placed them in a thermostatic chamber. In the examples of the present invention the applicant proceeded in this way, setting the temperature at 50° C. so as to be even more discriminating than in document EP 1 446 373. It thus obtained particularly stable pH values, by using monoethanolamine, diethanolamine and triethanolamine in step c) of the method according to the present invention.

Within the meaning of the present application, the term "stable composition" is therefore intended to mean a composition of which the pH does not significantly change, at 50° C., for a period at least equal to 1 month, preferentially 3 months, very preferentially 6 months, most preferably at least equal to 1 year.

Thus, a first subject of the present invention consists of a method for preparing a composition of internal dehydration product of a hydrogenated sugar, comprising:
a) a step of distilling a medium containing said internal dehydration product in order to obtain a distillate enriched in this product,
b) optionally, at least one subsequent step of purifying the distillate thus obtained, c) a subsequent step of bringing the distillate obtained during step a), and then optionally subjected to step b), into contact with an agent capable of improving the stability of the internal dehydration product predominantly contained in the distillate, d) optionally, a subsequent step of shaping the resulting composition of internal dehydration product of a hydrogenated sugar, and characterized in that the agent used in step c) is chosen from monoethanolamine, diethanolamine and triethanolamine, and mixtures thereof.

Preferably, the agent used in step c) is chosen from diethanolamine and triethanolamine, and mixtures thereof.

The method according to the invention is characterized in that the agent used in step c) is used in a proportion of from 0.0001% to 2%, preferentially from 0.001% to 2%, more preferentially from 0.002% to 1.5%, these percentages being expressed by dry weight of improving agent relative to the dry weight of the internal dehydration product of hydrogenated sugar then predominantly present in the distillate, for example isosorbide then present in this medium.

In the context of the method according to the invention, it should be specified that the medium subjected to the distilling step a) may be of very varied nature, including in terms of solids content, of temperature and/or of purity of the desired dehydration product. According to a first variant, it may be an isosorbide composition consisting of the medium resulting directly from the actual dehydration reaction and having a desired-product, for example isosorbide, purity of about 50% to 80%. According to another possibility, said composition may, due to the fact in particular that it already results from one or more prior purification operations, in particular by distillation and/or crystallization, have a desired-product, for example isosorbide, purity greater than 80%.

Advantageously, the distilling step a) is followed by a step b) of purifying the resulting distillate.

According to a first variant, step b) consists of a purifying step according to which the distillate, generally dissolved, is treated with at least one purification means chosen from decolorizing means and ionic exchange means.

The term "decolorizing means" is intended to mean in particular active carbon in granular or pulverulent form and adsorption resins. By way of example, use may be made, alone or in combination, of granular active carbon such as the product Ceca DC 50, of pulverulent active carbon such as the product Norit SX+ and/or of a resin such as those known as Duolite XAD 761, Macronet MN-600 or Macronet MN-400.

The term "ionic exchange means" is intended to mean in particular weak or strong anionic resins and weak or strong cationic resins. By way of example, use may be made, alone or in combination, of a strong anionic resin such as the Amberlite IRA 910 resin or a strong cationic resin such as the Purolite C 150 S resin. The ionic exchange means may advantageously comprise at least one anionic resin and at least one cationic resin. Preferably, this means is composed of a mixed bed of anionic and cationic resin(s) or of a succession of cationic then anionic resin(s) or of a succession of anionic then cationic resin(s).

Preferentially, during step b) of the method in accordance with the invention, the distillate obtained during step a) is treated in any order with at least one active carbon and with at least one ionic or nonionic resin. Very advantageously, said distillate is treated first with an active carbon, then with at least one resin and then again with an active carbon.

According to another variant of the method according to the invention, the applicant company found that it was particularly advantageous for the composition subjected to the purifying step b) to already have certain characteristics in terms of maximum content of particular impurities, for example of formic acid and of species of monoanhydrohexose type. It found, moreover, that such a content could in particular be guaranteed by directly subjecting the distillate obtained during step a) to said purifying step b).

The method according to the invention can therefore be characterized in that the distillate subjected to said step b) has a formic acid content of less than 0.002% and a monoanhydrohexose content of less than 0.02%, these percentages being expressed by dry weight relative to the dry weight of the internal dehydration product of hydrogenated sugar then predominantly present in said distillate, for example to the dry weight of isosorbide present in said distillate. The distillate may in particular have a formic acid content of less than 0.0005% and a monoanhydrohexose content of less than 0.005%.

According to another variant and advantageously, the improving agent used according to the invention is used directly after the purifying step b) and, in particular, as will moreover be exemplified, introduced directly onto the purified aqueous solution of internal dehydration product resulting from step b), which generally has a temperature at most equal to 60° C.

Whatever the operating mode of the method which is the subject of the invention, the applicant company also found that it could be advantageous for all or part of step c), during which the improving agent is present, to be carried out in a medium which is liquid and the temperature of which is at least equal to the softening or melting temperature of the desired internal dehydration product (for example isosorbide), but below approximately 140° C. This temperature may, in particular in the case of isosorbide, be between 60 and 135° C.

These conditions improve the homogeneous distribution of the improving agent within the resulting composition, in particular if said composition must be cooled and then shaped in accordance with optional step d).

The mixing of the distillate resulting from step a) with the stabilizing agent is extremely rapid since the amine used proves to be extremely soluble in the distillate, so that the duration of step c)—if it does not however last less than approximately one second—is not critical for the method in question.

After step c) and as previously indicated, the composition of internal dehydration product of a hydrogenated sugar obtained according to the invention can be shaped during a subsequent step d). This step can consist of an operation of pelletizing or flaking the crystalline mass or massed product resulting from the cooling, in particular by contact on a cold surface, of the composition resulting from step c).

The shaping step d) can, if desired, be followed by a milling and/or sieving step, this being before any step of storing and/or bagging of the composition thus obtained.

According to another variant, the composition of internal dehydration product of a hydrogenated sugar obtained according to the invention can, after step c) be stored as it is, in particular in the liquid or pasty state, without a subsequent specific shaping step.

The composition resulting from the method according to the invention may, moreover, have undergone, at any time, a concentrating step, in particular a step of evaporation under vacuum, said step being carried out under the mildest possible conditions, in particular in terms of time and temperature. This step then consists in concentrating said composition while keeping it in liquid form, in particular at a solids content of between 50% and 90%, preferentially between 75% and 88%. It can also consist in concentrating said composition so as to obtain a final product in dry form.

Preferably, it is most advantageous to carry out said concentrating step directly after step c).

All of the steps of the method according to the invention, obligatory or optional, which have just been described can also, if desired, be carried out under an inert atmosphere, including the characteristic step c) of the present invention and/or any subsequent step, in particular shaping, storing or bagging step.

In one preferred variant, the method according to the invention is characterized in that the internal dehydration product of a hydrogenated sugar is isosorbide.

Following this, a novel means is available which is capable of providing a composition of an internal dehydration product of a hydrogenated sugar, for example an isosorbide composition, the stability of which is improved, such a stability being required regardless of the uses for which said composition is intended and regardless, moreover, of the purity of said composition.

Thus, another subject of the present invention relates to a composition containing at least one internal dehydration product of a hydrogenated sugar, characterized in that it contains from 0.0001% to 2%, preferentially from 0.001% to 2%, more preferentially from 0.002% to 1.5% of an improving agent chosen from monoethanolamine, diethanolamine and triethanolamine, and mixtures thereof, and which is preferentially chosen from diethanolamine and triethanolamine, and mixtures thereof, these percentages being expressed by dry weight of improving agent relative to the dry weight of the internal dehydration product of hydrogenated sugar then predominantly present in said composition, for example, of isosorbide then present in this medium.

In one particular variant, this composition is characterized in that the internal dehydration product of a sugar is isosorbide.

In a first variant wherein the composition is in liquid form, it is characterized in that it has a solids content of between 50% and 90%, preferably of between 75% and 88%.

In a second variant, said composition is in solid form (said composition therefore having a solids content of 100%).

Such compositions can in particular be used for the preparation of polymeric or non-polymeric, biodegradable or non-biodegradable products or mixtures intended for the chemical, pharmaceutical, cosmetological or food industries.

The present invention will be described in even more detail by means of the examples which follow and which are no way limiting.

EXAMPLES

Example 1

This example relates to the production of an isosorbide composition according to the prior art (use of disodium phosphate) and according to the invention (use of monoethanolamine, diethanolamine and triethanolamine). It illustrates the increase in the duration of stability of said compositions in the context of the invention, through the monitoring of the pH of these compositions over time.

1 kg of a solution of sorbitol with a 70% solids content sold by the applicant under the name Neosorb 70/02 and 7 g of concentrated sulfuric acid are placed in a jacketed stirred reactor. The mixture obtained is heated under vacuum (pressure of approximately 100 mbar) for 5 hours so as to remove the water contained in the initial reaction medium and that originating from the sorbitol dehydration reaction.

The reaction crude is then cooled to around 100° C. and then neutralized with 11.4 g of a 50% sodium hydroxide solution. The isosorbide composition thus neutralized is then distilled under vacuum (pressure below 50 mbar).

The crude isosorbide distillate, which is slightly colored (pale yellow color), is then dissolved in 2-propanol, at a temperature of 60° C., so as to obtain a solution with a 75% solids content. This solution is then slowly cooled, in the space of 5 hours, to a temperature of 10° C.; a recrystallized isosorbide seed is added at 40° C.

The crystals are then drained in a centrifuge and washed with a small amount of 2-propanol. After drying under vacuum, the crystals are redissolved in water so as to obtain a solids content of 40%.

This solution is then percolated on a column of granular active carbon CPG 12-40 at a rate of 0.5 BV/h (Bed Volume/hour). The decolorized isosorbide composition thus obtained is then passed, at a rate of 2 BV/h, successfully over a column of Purolite C 150 S strong cationic resin and then a column of Amberlite IRA 910 strong anionic resin. This solution is then treated with powdered active carbon of Norit SX+ type at 20° C. for 1 hour. The active carbon is used in a proportion of 0.5% expressed by dry weight/dry weight of solution.

The agent to be tested, that is to say:
0.005% of disodium phosphate (dry weight/dry weight of isosorbide contained in the composition) for test No. 1;
0.0025% of monoethanolamine (dry weight/dry weight of isosorbide contained in the composition), for test No. 2;
0.0025% of diethanolamine (dry weight/dry weight of isosorbide contained in the composition), for test No. 3;
0.0025% of triethanolamine (dry weight/dry weight of isosorbide contained in the composition), for test No. 4;
is then introduced into said composition.

After filtration, the isosorbide solution is concentrated under vacuum. The molten mass obtained crystallizes on cooling in the form of a massed product of large crystals which is subsequently ground to obtain a white-colored powder having a moisture content of 0.2%.

200 g of this isosorbide massed product are directly introduced into a glass container having a volume of 500 ml which, after having been hermetically closed, is placed in an oven maintained at 50° C.

For each of the flasks corresponding to tests No. 1, 2, 3 and 4, the change in pH over time is monitored. The results appear in table 1. The pH measurement is carried out on a Radiometer Analytical PHM 220 pH-meter equipped with a Mettler Toledo combined Ag/AgCl wire electrode, calibrated beforehand using pH 7 and 4 buffer solutions. The pH is measured on a sample of product dissolved at 40% by weight of solids content in osmosed water.

It is clearly verified that only tests No. 2, 3 and 4 have a pH which is advantageously stable over time for at least 3 months, it being possible for this period to reach 6 months in the case of tests No. 3 and 4 corresponding to diethanolamine and to triethanolamine.

TABLE 1

| | Agent according to step c) | | | | | | pH | | | | |
|---|---|---|---|---|---|---|---|---|---|---|---|
| Test No. | Nature | Amount (% dry/dry) | t = 0 | t = 1 month | t = 1.5 months | t = 2 months | t = 2.5 months | t = 3 months | t = 4 months | t = 5 months | t = 6 months |
| 1 | disodium phosphate | 0.005 | 7.9 | 7.8 | 7.9 | 7.7 | 3.3 | | | | |
| 2 | monoethanol-amine | 0.0025 | 7.4 | 7.3 | | 6.8 | | | 6.9 | 3.2 | |
| 3 | diethanol-amine | 0.0025 | 7.8 | 7.6 | | 7.5 | | 7.5 | 7.5 | 7.5 | 7.5 |
| 4 | triethanol-amine | 0.0025 | 7.9 | 7.7 | | 8 | | 7.9 | 7.7 | 7.7 | 7.8 |

Example 2

This example relates to the production of an isosorbide composition according to the prior art (use of sodium hydroxide, of ascorbic acid, of tocopherol, of sodium metaborate, of morpholine and of butylated hydroxy-toluene) and according to the invention (use of diethanolamine and triethanolamine). It illustrates the increase in the duration of stability of said compositions in the context of the invention, through the monitoring of the pH according to a protocol identical to that described in the previous example.

The only difference lies in the fact that the oven is maintained at 60° C., thereby making the tests much more discriminating, it being possible for differences to be observed over a period of a few days.

The results appear in table 2.

It is thus clearly shown that the best stabilities are obtained for diethanolamine and triethanolamine.

TABLE 2

| Stabilizing agent | DEA | TEA | NaOH | Ascorbic acid | Tocopherol | Na metaborate | Morpholine | BHT |
|---|---|---|---|---|---|---|---|---|
| T = 0 | 8.3 | 7.7 | 9.1 | 4.9 | 5.3 | 8.5 | 7.9 | 6.9 |
| T = 2 days | 8.6 | 8.0 | 8.0 | 4.3 | 3.5 | 8.6 | 7.8 | 3.9 |
| T = 3 days | 8.5 | 8.0 | 8.0 | 3.9 | 3.3 | 7.9 | 7.2 | 3.5 |
| T = 5 days | 8.0 | 8.0 | 7.4 | 3.5 | 3.2 | 7.7 | 7.1 | 3.4 |

The invention claimed is:

1. A method for preparing a composition of internal dehydration product of a hydrogenated sugar, comprising:
    a) a step of distilling a medium containing said internal dehydration product in order to obtain a distillate enriched in this product,
    b) optionally, at least one subsequent step of purifying the distillate thus obtained,
    c) a subsequent step of bringing together the distillate obtained during step a), and then optionally subjected to step b), and an agent capable of improving the stability of the internal dehydration product predominantly contained in the distillate, said agent not being in gaseous form,
    d) optionally, a subsequent step of shaping the resulting composition of internal dehydration product of a hydrogenated sugar,
    and wherein the agent used in step c) is chosen from monoethanolamine, diethanolamine and triethanolamine, and mixtures thereof.

2. The method as claimed in claim 1, wherein the agent used in step c) is chosen from diethanolamine and triethanolamine, and mixtures thereof.

3. The method as claimed in claim 1, wherein the agent used in step c) is used in a proportion of from 0.0001% to 2%, these percentages being expressed by dry weight of improving agent relative to the dry weight of the internal dehydration product of hydrogenated sugar then predominantly present in the distillate.

4. The method as claimed in claim 1, wherein the distilling step a) is followed by a purifying step b), during which the distillate is treated, in any order, with at least one activated carbon and with at least one ionic or nonionic resin.

5. The method as claimed in claim 1, wherein it comprises at least one concentrating step.

6. The method as claimed in claim 1, wherein the internal dehydration product of a hydrogenated sugar is isosorbide.

7. A composition containing at least one internal dehydration product of a hydrogenated sugar, containing from 0.0001% to 2%, of an improving agent chosen from monoethanolamine, diethanolamine and triethanolamine, and mixtures thereof, these percentages being expressed by dry weight of improving agent relative to the dry weight of the internal dehydration product of hydrogenated sugar then predominantly present in said composition.

8. The composition as claimed in claim 7, wherein the internal dehydration product of a hydrogenated sugar is isosorbide.

9. The composition as claimed in claim 7, wherein it has a solids content of between 50% and 90%.

10. The composition as claimed in claim 7, wherein it has a solids content of 100%.

11. Polymeric or non-polymeric, biodegradable or non-biodegradable products and mixtures intended for the chemical, pharmaceutical, cosmetological or food industries, prepared from the composition as claimed in claim 7.

* * * * *